United States Patent [19]
Sobel et al.

[11] Patent Number: 5,655,652
[45] Date of Patent: Aug. 12, 1997

[54] CENTER DISPENSE SUTURE PACKAGE

[75] Inventors: Martin Sobel, Flemington, N.J.; Robert James Cerwin, Pipersville; David Demarest, Morrisville, both of Pa.; Anthony Esteves, Somerville, N.J.; Robert A. Daniele, Flemington, N.J.; Joseph Siernos, Whitehouse Station, N.J.

[73] Assignee: Ethicon, Inc., Somerville, N.J.

[21] Appl. No.: 623,518

[22] Filed: Mar. 28, 1996

Related U.S. Application Data

[63] Continuation of Ser. No. 386,619, Feb. 10, 1995, abandoned.

[51] Int. Cl.$^6$ .................................................. A61B 17/06
[52] U.S. Cl. ........................... 206/63.3; 206/480; 206/477
[58] Field of Search .................................... 206/63.3, 225, 206/380, 388, 477, 480, 483; 220/307, 4.21

[56] References Cited

U.S. PATENT DOCUMENTS

| | | | |
|---|---|---|---|
| 3,485,436 | 12/1969 | Mirasol, Jr. | 220/307 X |
| 3,654,675 | 4/1972 | Peterson | 220/307 X |
| 3,768,638 | 10/1973 | Clarke | 220/307 X |
| 3,972,418 | 8/1976 | Schuler et al. | 206/63.3 |
| 4,961,498 | 10/1990 | Kalinski | 206/339 |
| 4,967,902 | 11/1990 | Sobel et al. | 206/63.3 |
| 5,052,551 | 10/1991 | Cerwin | 206/63.3 |
| 5,213,210 | 5/1993 | Cascio et al. | 206/63.3 X |
| 5,230,424 | 7/1993 | Alpern et al. | 206/63.3 |

*Primary Examiner*—M. D. Patterson
*Attorney, Agent, or Firm*—Emil Richard Skula

[57] ABSTRACT

A suture package having a base, an upwardly extending wall, an inner dispensing wall, a suture channel between the walls, and a top friction plate member mounted therein. The package has a central needle park and a discharge opening in the friction plate for removing a needle and suture from the package.

38 Claims, 4 Drawing Sheets

CENTER DISPENSE SUTURE PACKAGE

This is a continuation of application Ser. No. 08/386,619, filed Feb. 10, 1995, now abandoned.

TECHNICAL FIELD

The field of art to which this invention relates is packaging, in particular, packages for surgical needles and sutures.

BACKGROUND OF THE INVENTION

Packages for surgical needles and sutures are well known in the art. Conventional packages may consist of foldable cardboard or paper having a plurality of foldably connected panels for receiving sutures. Such packages typically have needle parks for mounting needles. The packages are designed to protect the needles and sutures during sterilization shipping and handling. The packages are further designed to provide ease of removal of the needles and sutures. Conventional plastic packages are also available for surgical needles and sutures. The plastic packages typically have an oval shape or circular shape with a peripheral suture channel for containing one or more sutures. A needle park is typically positioned interior to the channel for mounting surgical needles. The plastic packages are believed to have several advantages over paper packages in that they are easy to load, tend to maintain the suture in a controlled position within the channel, and provide ease of dispensing. Suture packages having channels for containing sutures are disclosed in the following U.S. patents which are incorporated herein by reference: U.S. Pat. No. 4,967,902; U.S. Pat. No. 5,052,551; U.S. Pat. No. 4,967,902; U.S. Pat. No. 5,131,533; U.S. Pat. No. 5,213,210; U.S. Pat. No. 4,961,498.

Although the packages of the prior art are known to function appropriately in containing surgical sutures and needles, there is a constant need in this art for improved suture packages. In particular, there is a need for a suture package having a suture channel which can be readily utilized in automated suture winding apparatuses. There is a further need in this art for a suture package having a suture channel which has the capability of reducing the incidence of suture "lock-ups" when attempting to withdraw sutures from the package.

DISCLOSURE OF THE INVENTION

Therefore, it is an object of the present invention to provide an improved suture package having a suture channel which is easy to use in an automated suture winding process.

It is a further object of the present invention to provide a suture package having a suture channel which decreases the incidence of suture "lock-ups" when sutures are withdrawn from the package.

Accordingly, a suture package is disclosed. The suture package has a substantially flat base member. The base member has a top side, a bottom side, and an outer periphery. An outer wall extends upwardly from the top of the base member about its outer periphery. The outer wall has a top, an inner side, and an outer side. A flange member extends inwardly from the top of the outer wall. The flange member has a top and a bottom. An inner dispensing wall extends up from the top of the base member. The inner dispensing wall has an inner side, an outer side, and a top, preferably rounded. The package has a channel for receiving a suture. The suture channel is formed between the outer side of the inner dispensing wall, the inner side of the outer wall, and the top of the base member. The inner dispensing wall, as well as the flange member, may be segmented. A needle park is positioned on the top side of the flat base member, interior to the inner dispensing wall. A flat, friction plate member is mounted in the package. The flat, friction plate member has a top, a bottom, a suture exit opening and an outer periphery. The flat friction plate has a biasing section for engaging the bottom of the flange and/or the inner side of the outer wall such that the friction plate is engaged within the package below the flange member and the bottom of the friction plate is biased against the top of the inner dispensing wall. Preferably, the friction plate member has a plurality of radially extending slots about its periphery.

Yet another aspect of the present invention is a suture package having substantially flat base member. The base member has a top side, a bottom side, and an outer periphery. An outer wall extends upwardly from the top of the base member about its outer periphery. The outer wall has a top, an inner side, and an outer side. A groove is contained in the outer wall for receiving the periphery of a friction plate member. An inner dispensing wall extends up from the top of the base member. The inner dispensing wall has an inner side, an outer side, and a top, preferably rounded. The inner dispensing wall may be segmented. The package has a channel for receiving a suture. The suture channel is formed between the outer side of the inner dispensing wall, the inner side of the outer wall, and the top of the base member. A needle park is positioned on the top side of the flat base member, interior to the inner dispensing wall. A flat, friction plate member is mounted in the package. The flat, friction plate member has a top, a bottom, a suture exit opening and an outer periphery. The flat friction plate has a biasing section for engaging the bottom of the flange and/or the inner side of the outer wall such that the friction plate is engaged within the package below the flange member and the bottom of the friction plate is biased against the top of the inner dispensing wall. Preferably, the friction plate member has a plurality of radially extending slots about its periphery.

A needle and suture combination is removed from the packages of the present invention by initially removing the needle from the needle park and pulling the needle and suture through the exit opening in the friction plate. The friction plate member is a "floating" member in that it is capable of limited vertical displacement. The "floating" friction plate member allows a suture to exit the channel over the top of the inner wall by forcing the floating friction plate member to displace vertically. Preferably, the friction plate member contains a plurality of radially extending slots.

Yet another aspect of the present invention, is either of the above-described packages without a needle park.

The foregoing and other features and advantages of the present invention will become more apparent from the following description and accompanying drawings.

BEST MODE FOR CARRYING OUT THE INVENTION

Figure 1:
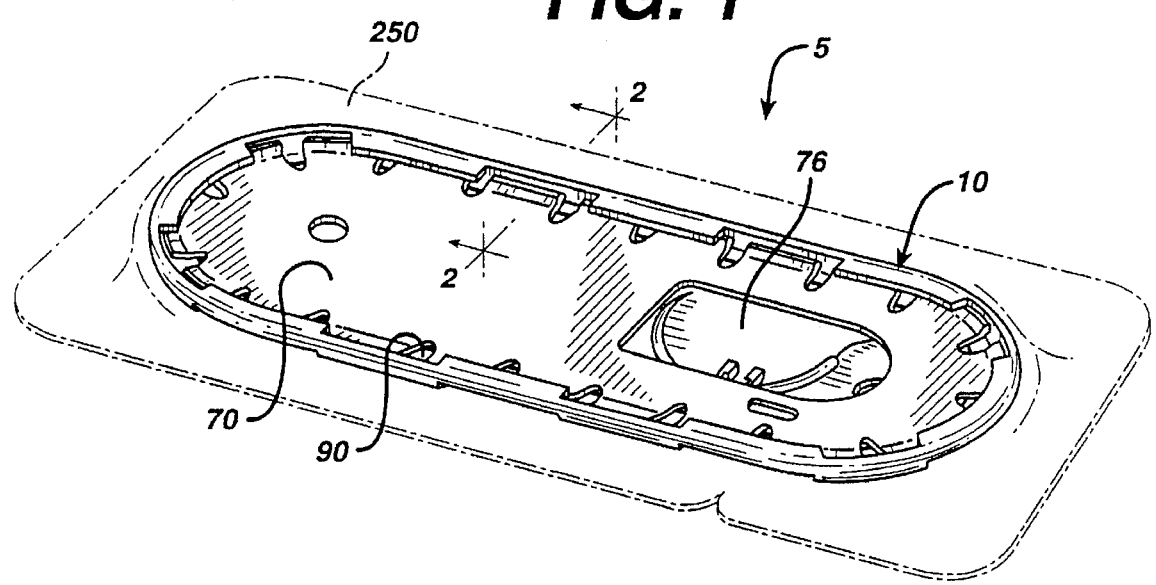
FIG. 1 is a perspective view of a package of the present invention; an outer overwrap package is shown in phantom.

Referring to FIGS. 1–6, the suture package 5 of the present invention is illustrated. The suture package 5 is seen to have tray 10 and friction plate member 70. The tray 10 is seen to have flat base member 20. The flat base member 20 is seen to have top 21, bottom 22, and outer periphery 24. The flat base member 20 is seen to have a generally oval configuration wherein opposed, substantially parallel, longitudinal sides are connected by opposed semi-circular end sections; however, the flat base member may have other configurations including other oval configurations, circular configurations, polygonal configurations, combinations thereof and the like. The base member 20 is seen to contain a plurality of holes 25 and mounting pin holes 26 and 27.

Extending upwardly from the top of the flat member 20 about the periphery 24 is the outer wall 30. The outer wall 30 is seen to have top 32, inner surface 34, and outer surface 35. Extending inwardly from the top 32 of the wall 30 are the flange members 40 separated by gaps 49. The flange members 40 are seen to have top 41 and bottom 42. The flange members 40, if desired, may be replaced by one continuous flange member rather than having segmented members.

Figure 2:
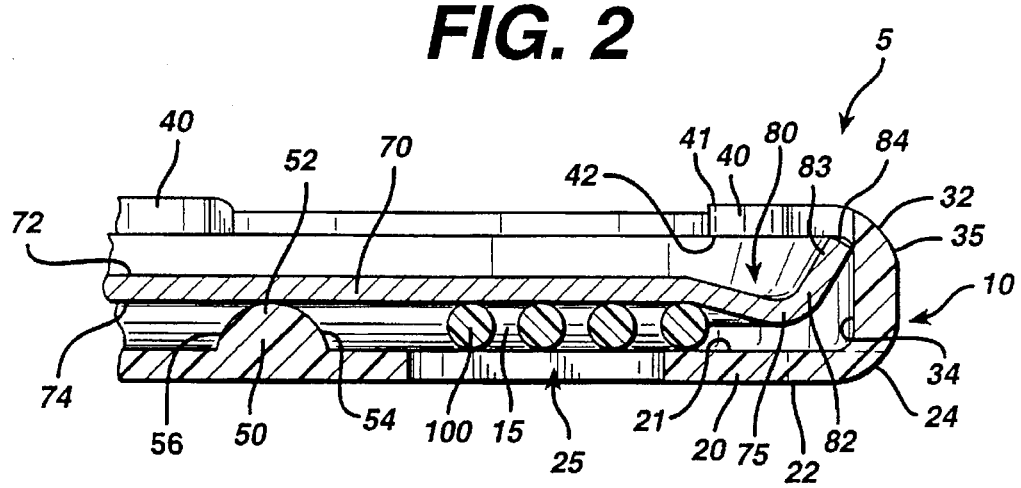
FIG. 2 is a partial cross-section of the package of FIG. 1 taken along view line 2—2.

Extending upwardly from the top 21 of the base member 20 is the inner dispensing wall 50. The inner dispensing wall 50 is seen to have top 52 and outer surface 54 and inner surface 56. It is preferred that the dispensing wall 50 have a curved cross-sectional configuration. The cross-sectional configuration of wall 50 may be semi-circular as illustrated in FIG. 2, or other curved configurations may be utilized including oval, parallel sides with a curved top, combinations thereof and the like. Although not preferred, if one skilled in the art were willing to accept any disadvantages attendant therewith, the cross-section of dispensing wall 50 could be square, polygonal, rectangular, triangular, etc. The inner dispensing wall 50 is preferably segmented, wherein segments 51 are separated by gaps 59. However, the wall 50 may be continuous with one or more optional suture exit openings if desired. The suture dispensing wall 50 will typically have the same configuration as the base member 20, but may have other configurations if desired. Preferably, the inner wall 50 and the outer wall 30 are parallel or separated by a constant distance. A suture channel 15 for receiving and retaining a suture 100 is formed by the inner surface 34 of outer wall 30, the outer surface 54 of inner wall 50, and the top 21 of flat member 20.

Figure 3:
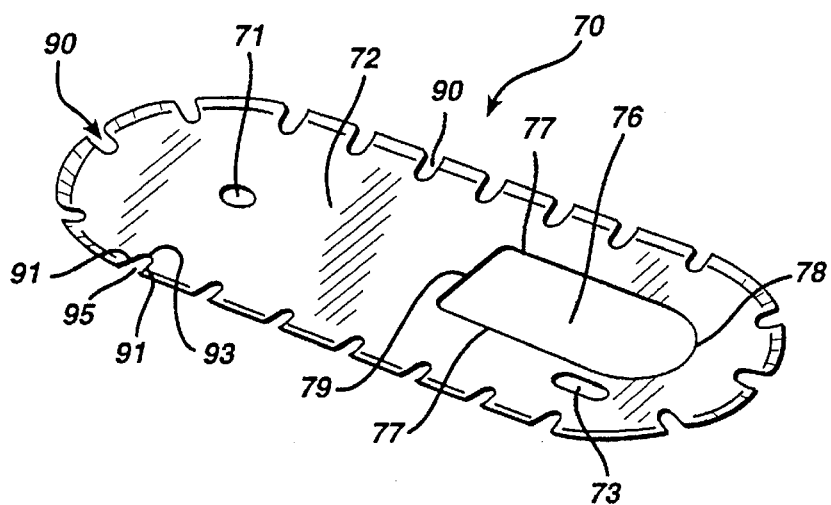
FIG. 3 is a top view of a preferred embodiment of a friction plate member useful in the package of the present invention; the friction plate member has a plurality of radial slots disposed about its periphery.
Figure 7:
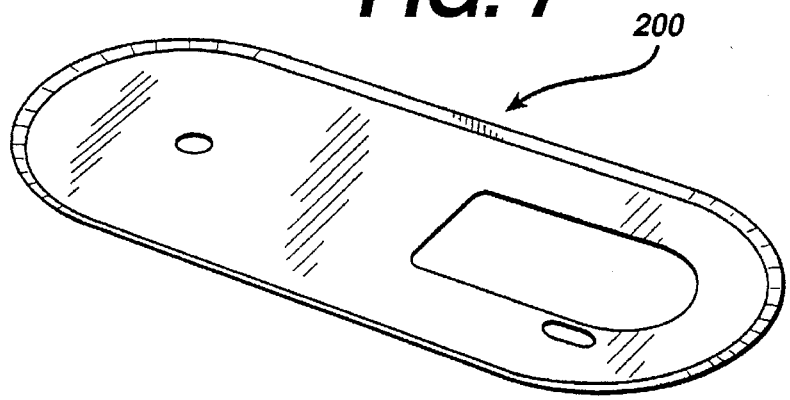
FIG. 7 is a perspective view of an alternate embodiment of a friction plate member which does not contain radial slots.

Mounted in the tray 10 is the friction plate member 70 (see FIG. 3). Friction plate member 70 is a substantially flat member having a top 72, a bottom 74, and an outer periphery 75. The friction plate member 70 is seen to have a suture discharge opening 76. Opening 76 is seen to have opposed sides 77, curved end 78, and opposed flat end 79. Opening 76 may have any suitable geometric configuration, including oval, circular, polygonal, rectangular, square and the like and combinations thereof. Friction plate member is seen to have alignment hole 71 and alignment hole 73 for aligning the friction plate member 70 to the tray 10. Friction plate member 70 is also seen to have a plurality of radially extending slots 90 in periphery 75. Slots 90 are seen to have oppose sides 91, rounded ends 93 and openings 95. The friction plate member 70 is seen to preferably have a configuration which is substantially oval and which is substantially identical to the configuration of the outer wall 30, although other configurations may be used. An alternate embodiment of the friction plate 70 is seen in FIG. 7. As seen in FIG. 7, plate member 200 is similar in configuration to plate member 70 but does not have radial slots about its periphery.

Figure 6:
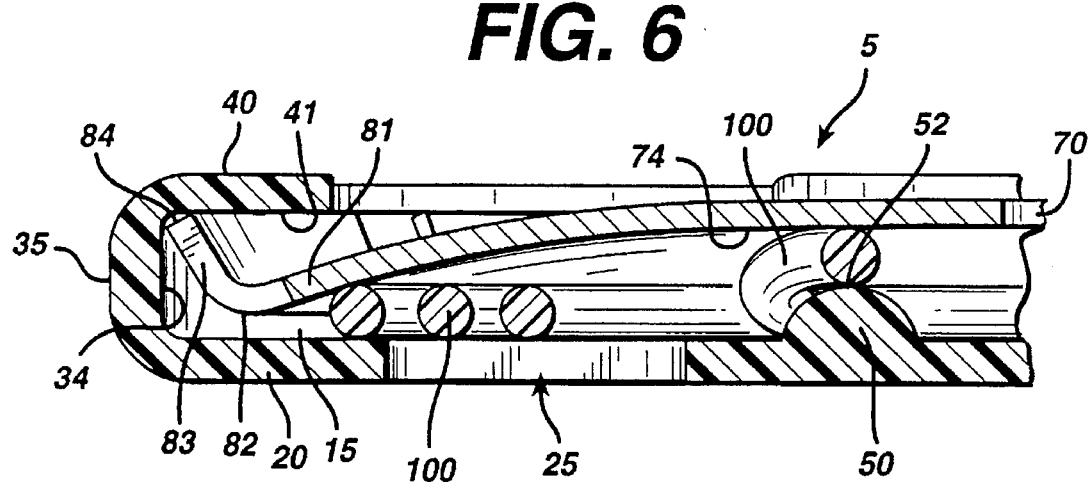
FIG. 6 is a partial side view taken along View Line 6—6 illustrating deflection of the friction plate as a suture is withdrawn over the inner dispensing wall.

Contained in the periphery 75 of the friction plate 70 is the peripheral locking flange rim 80. Referring to FIGS. 2 and 6, the peripheral locking flange rim 80 is formed when the friction plate member 70 is inserted into tray 10 thereby bending the part or all of outer periphery 75 of the friction plate member 70 to produce a curved rim 80 having downwardly extending section 81, an apex 82, and then upwardly and outwardly extending section 83. The end 84 of the rim 80 is seen to engage the inner surface 42 of the flange 40 and the inner surface 34 of the outer wall 35 thereby providing a downward bias by member 70 upon the top 52 of the inner wall 50, although the rim 80 may be designed to engage either surface solely. If desired, the biasing rim 80 could be replaced by equivalent structures that would provide a biasing force including elastomeric members, polymeric members, mechanical members such as springs, combinations and equivalents thereof, and the like. In order to cause rim 80 to be formed when inserting plate 70 into tray 10, it is necessary that the outer overall dimensions of plate 70 be sufficiently larger than the inner dimension of the inner surface 34 of outer wall 40 to effectively result in the desired bending to form rim 80. That is, there should be sufficient overhang to effectively produce the desired bending to form rim 80. If desired, rim 80 may be formed prior to insertion into tray 10 using conventional die forming techniques.

Figure 8:
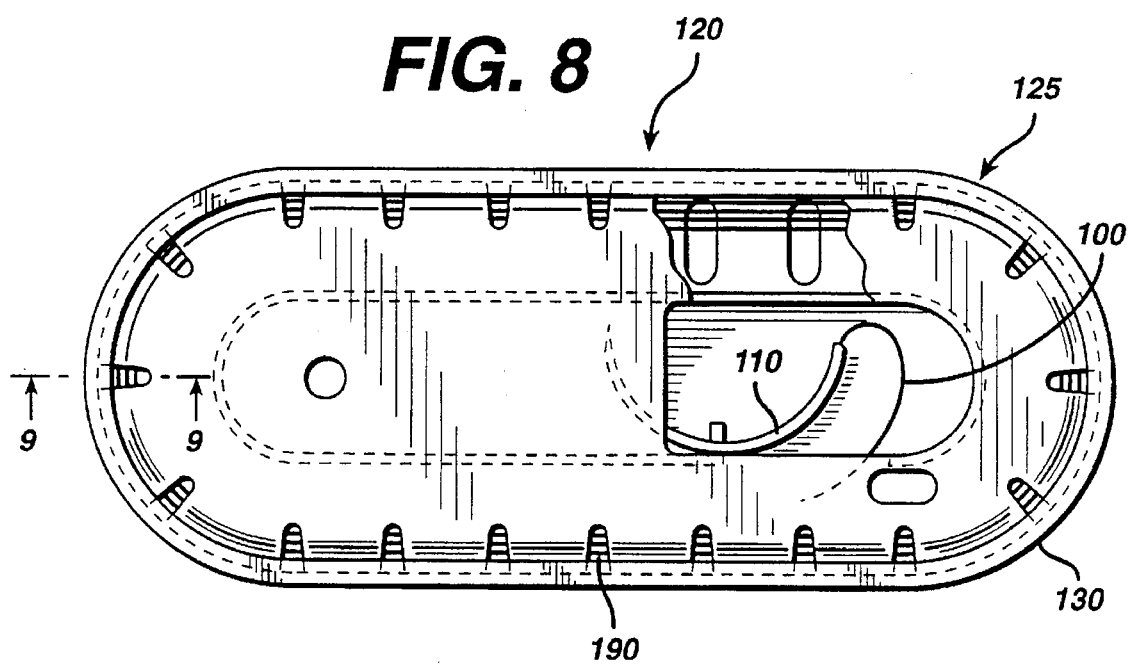
FIG. 8 is a top view of an alternate embodiment of the package of the present invention wherein the outer wall has a snap groove to retain the friction plate member.
Figure 9:
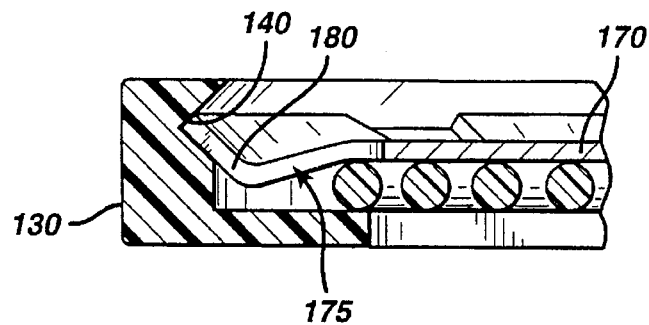
FIG. 9 is a partial side view taken along View Line 9—9 of the package of FIG. 8 illustrating the snap groove.

Referring to FIGS. 8 and 9, an alternate embodiment of the package of the present invention is illustrated. The package 120 is seen to have tray 125 and outer wall 130 having continuous snap groove 140 in lieu of a flange member for receiving the rim 180 of friction plate member 170. The friction plate member 170 is seen to have a plurality of radially extending slots 190 in the periphery 175 of the member 170. The friction plate member 170 is seen to have rim section 180. Groove 140 may have any cross-section sufficient to effectively retain rim 180 including intersecting planar surfaces, curved surfaces, combinations thereof and the like.

The needle park 60 is seen to be positioned on the top 21 of the base member 20 interior to the inner dispensing wall 50 such that a surgical needles 110 mounted in needle park 60 can be withdrawn through discharge opening 76 in friction plate 70. The needle park 60 is seen to preferably consist of two pairs of opposed members 62 having deformable edges 63, the members 62 extend from or are mounted to the top 21 of base member 20. The needle park 60 may also consist of conventional needle parks including foam members, flaps, and the like and equivalents thereof.

Figure 4:
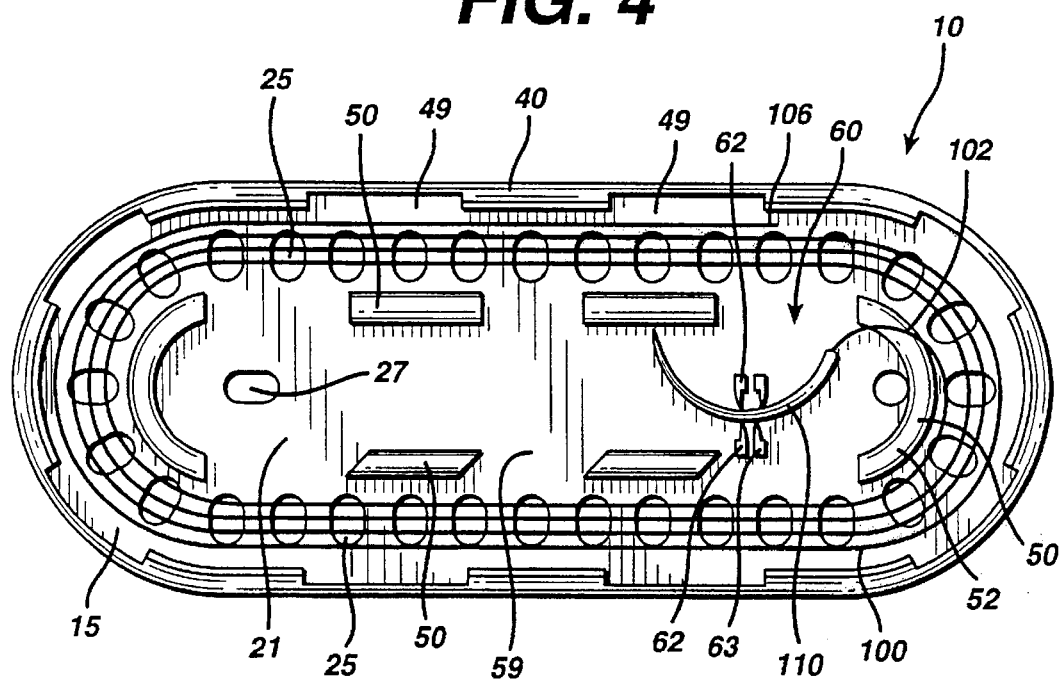
FIG. 4 is a top view of the package of a present invention with the friction plate member removed, illustrating a tray containing a suture in the channel along with a surgical needle mounted in the needle park.

Referring to FIG. 4, the base member 20 is seen to have holes 26 and 27 for receiving conventional mounting pins during the winding process. The base member 20 is also seen to have a plurality of holes 25 in channel 15 for receiving conventional winding pins. The holes 25 also serve as vacuum ports in order to draw a vacuum upon the base member 20 as sutures 100 are being loaded into the channel 15.

A conventional surgical needle 110 and suture 100 combination is wound into tray 10 of the present invention in the following manner (see FIG. 4). The tray 10 is mounted to a conventional winding fixture wherein conventional mounting pins are inserted through mounting holes 26 and 27. In addition, conventional winding pins are inserted through the holes 25 in the channel 15 of base member 20. At the same time, a vacuum is drawn upon the holes 25. Then, a surgical needle is mounted into the needle park 60 between the edges 63 of edges 62. Next, a distal end section 102 of the suture 100 is preferably placed across the top 52 of a section of inner dispensing wall 50. Then the suture 100 is wound in channel 15, preferably in an arranged wind pattern such that adjacent coils of suture are separated by a gap and no coils of suture 100 cross each other. After winding, the friction plate member 70 is snapped into tray 10 to form package 5 such that rim 80 preferably engages the underside or bottom 42 of flange member 40 and the inner surface 34 of outer wall 30. Referring to FIG. 4, the suture 110 is seen to have distal end or tail 106. A suture 100 and needle 110 are similarly wound into package 120 as seen in FIGS. 8 and 9. Friction plate member 170 is snapped into tray 125 such that flange member 180 engages the snap groove 140 utilizing alignment holes 71 and 73, and conventional alignment rods which fit into the holes 71 and 73 and guide the plate 70 into tray 10.

The surgical needle 110 and suture 100 are withdrawn from the packages of the present invention in the following manner. The needle 110 is grasped with a conventional needle grasper and withdrawn through opening 76 friction plate member 70. Pulling on the needle 110 thusly causes the suture 100 to uncoil and be withdrawn either through a gap 59 in inner dispensing wall 50 or between the top 52 of inner dispensing wall 50 and the bottom 74 of friction plate member 70, and through opening 76 (See FIG. 4). The needle 110 and suture 100 are withdrawn for package 120 in a similar manner.

Figure 5:
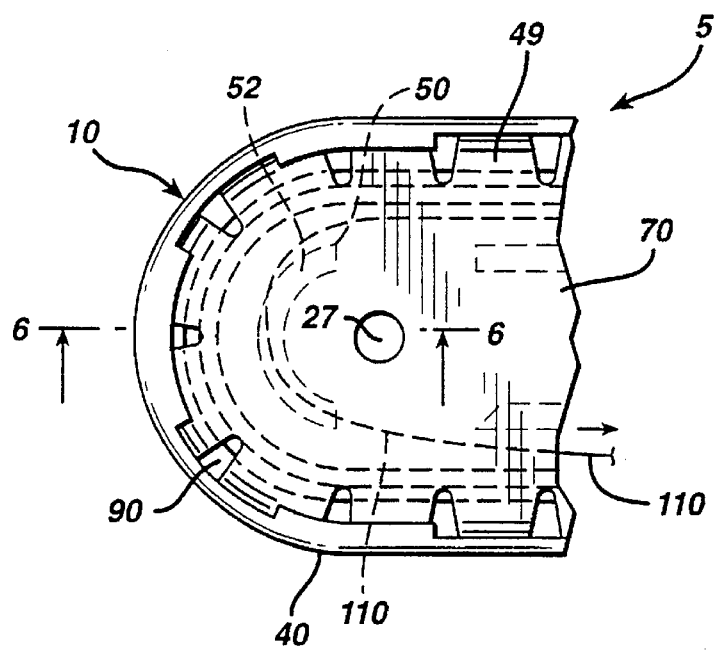
FIG. 5 is a partial top view of the package of FIG. 1 illustrating a suture in phantom in the package and a potential path of movement of the suture when it is withdrawn.

The suture packages of the present invention are believed to resist suture "lock-ups" in the following manner. The bottom 71 of friction plate member 70 is biased against the top 52 of inner wall 50 such that the friction plate is maintained in a "floating" mode capable of vertical displacement. As seen in FIGS. 5 and 6, a suture 100 rather than locking-up in channel 15 about inner wall 50 can move or slide up and across the top 52 of wall 50 below the bottom 74 of friction plate 70 by forcing the friction plate 70 upward, and the suture 100 can then exit through suture discharge port or opening 76. Package 120 functions in the same manner. The term suture "lock-up" is defined to mean a situation which may occur when attempting to withdraw a suture form a suture package having an oval, circular, or curved suture channel wherein the suture wraps around a core, inner wall, pin, etc., thereby preventing suture withdrawal. Although not desiring to be held to any particular theory, it is believed that a "lock-up" experienced upon suture withdrawal may be caused by a capstan effect.

The trays of the present invention may be constructed of conventional materials including medical grade cardboard or polymers or combinations thereof. It is preferred to use polymers.

The trays of the present are typically manufactured from conventional polymers using conventional processes including injection molding, vacuum forming, numerically controlled machining, and standard machining techniques.

The friction plate members of the present invention may be constructed of conventional medical grade materials such as cardboard or plastic. The friction plate members are preferably manufactured using conventional manufacturing processes including die cutting and forming.

The surgical needles 110 which can be packaged in the packages of the present invention include any conventional surgical needles including tapered point and cutting point needles. The needles 100 may have curved, semi-curved, straight configurations, and other conventional configurations. The sutures 100 which may be packaged in the packages of the present invention include any of the conventional sutures, absorbable and non-absorbable, such as silk, polypropylene, polydioxanone, and the like and equivalents thereof. The sutures may be braided, woven or monofilament. The sutures are typically mounted to the ends of surgical needles by conventional processes such as swaging.

The suture packages of the present invention are typically packaged in an outer package, such as outer package 250 seen in FIG. 1, to maintain the sterility of the packages and their contents. The outer package 250 may be any conventional outer package including foil packages, polymer film, paper, laminates, combinations thereof, and the like. The packages 5 of the present invention are sterilized using conventional sterilization processes including ethylene oxide, radiation, heat, and the like. The packages of the present invention containing needles 110 and sutures 100 may be sterilized prior to or after packaging in an outer package, depending on the type of outer package used and further depending upon the type of sterilization process utilized.

The suture packages of the present invention have many advantages. The packages can dispense a broad range of suture types and lengths. The packages are adapted to be used on automatic suture loading apparatuses. In addition, the packages of the present invention reduce the incidence of suture "lock-ups".

Although this invention has been shown and described with respect to detailed embodiments thereof, it will be understood by those skilled in the art that various changes and forming detail may be made without departing from the spirit and scope of the claimed invention.

We claim:

1. A suture package, comprising:
   a substantially flat base member having a top side, a bottom side, and an outer periphery;
   an outer wall extending upwardly from the top of the base member about the periphery of the base member, said outer wall having a top, an outer surface, and an inner surface;
   an inner dispensing wall extending up from the top of the base member said inner wall having an inner side and a top and an outer side and an outer surface, wherein said outer surface of the dispensing wall and said inner surface of the outer wall and the top of the base member form an endless oval channel for receiving a suture;
   a suture wound into the channel, such that the suture comprises adjacent coils which do not overlap;
   a flange member extending inwardly from the top of the outer wall, said flange member having a top and a bottom;

a needle park means for receiving a needle, said needle park means centrally mounted to the top of the base member within the inner wall; and, a flat, floating, plate member having a top, a bottom, a central suture discharge opening, and an outer periphery, the flat friction plate additionally having biasing means about the outer periphery, wherein the flat plate member is mounted on the top of the inner dispensing wall and below the flange member such that the bottom of the plate member is biased against the top of the inner wall by the biasing means, and wherein the bottom of the plate member is biased against the suture coils;

wherein a suture loaded into the channel is removable through the central discharge opening by displacing the floating plate such that the suture moves between the bottom of the floating plate and the top of the inner wall.

2. The package of claim 1 wherein the biasing means comprises an outwardly extending rim which is curved.

3. The package of claim 1 additionally comprising a surgical needle and suture.

4. The package of claim 3, wherein said package and needle and suture are sterile.

5. The package of claim 4 further comprising a sealed outer package.

6. The package of claim 1 wherein the friction plate member additionally comprises a plurality of radially slots extending into the periphery, wherein the slots have an open end and a closed end.

7. The package of claim 1 wherein the flange member comprises a plurality of segments separated by spaces.

8. The package of claim 1 wherein the inner wall comprises segments separated by spaces.

9. The package of claim 1 wherein the inner wall has a semi-circular cross-section.

10. The package of claim 1 wherein the channel has an oval configuration.

11. A suture package, comprising:

a substantially flat base member having a top side, a bottom side, and an outer periphery;

an outer wall extending upwardly from the top of the base member about the periphery of the base member, said outer wall having a top, an outer surface, and an inner surface;

an inner dispensing wall extending up from the top of the base member said inner wall having an inner side and a top and an outer side and an outer surface, wherein said outer surface of the dispensing wall and said inner surface of the outer wall and the top of the base member form an endless oval channel for receiving a suture;

a suture wound into the channel, such that the suture comprises adjacent coils which do not overlap;

a flange member extending inwardly from the top of the outer wall, said flange member having a top and a bottom; and, a flat, floating plate member having a top, a bottom, a central suture discharge opening, and an outer periphery, the flat friction plate additionally having biasing means about the outer periphery, wherein the flat plate member is mounted on the top of the inner dispensing wall and below the flange member such that the bottom of the plate member is biased against the top of the inner wall by the biasing means, and wherein the bottom of the plate member is biased against the suture coils, wherein a suture loaded into the channel is removable through the central discharge opening by displacing the floating plate such that the suture moves between the bottom of the floating plate and the top of the inner wall.

12. The package of claim 11 wherein the biasing means comprises an outwardly extending rim which is curved.

13. The package of claim 11 additionally comprising a surgical needle and suture.

14. The package of claim 13, wherein said package and needle and suture are sterile.

15. The package of claim 14 further comprising a sealed outer package.

16. The package of claim 11 wherein the friction plate member additionally comprises a plurality of radially slots extending into the periphery, wherein the slots have an open end and a closed end.

17. The package of claim 11 wherein the flange member comprises a plurality of segments separated by spaces.

18. The package of claim 11 wherein the inner wall comprises segments separated by spaces.

19. The package of claim 11 wherein the inner wall has a semi-circular cross-section.

20. The package of claim 11 wherein the channel has an oval configuration.

21. A suture package, comprising:

a substantially flat base member having a top side, a bottom side, and an outer periphery;

an outer wall extending upwardly from the top of the base member about the periphery of the base member, said outer wall having a top, an outer surface, and an inner surface;

an inner dispensing wall extending up from the top of the base member said inner wall having an inner side and a top and an outer side and an outer surface, wherein said outer surface of the dispensing wall and said inner surface of the outer wall and the top of the base member form an endless oval channel for receiving a suture;

a suture wound into the channel such that the suture compresses adjacent coils which do not overlap, a snap groove extending into the inner surface of the outer wall;

a needle park means for receiving a needle, said needle park means centrally mounted to the top of the base member within the inner wall; and, a flat, floating plate member having a top, a bottom, a central suture discharge opening, and an outer periphery, the flat friction plate additionally having biasing means about the outer periphery, wherein the flat plate member is mounted on the top of the inner dispensing wall and the periphery of the plate member engages the snap groove such that the bottom of the plate member is biased against the top of the inner wall by the biasing means, and wherein the bottom of the plate member is biased against the suture coils;

wherein a suture loaded into the channel is removable through the central discharge opening by displacing the floating plate such that the suture moves between the bottom of the floating plate and the top of the inner wall.

22. The package of claim 21 wherein the biasing means comprises an outwardly extending rim which is curved.

23. The package of claim 21 additionally comprising a surgical needle and suture.

24. The package of claim 23, wherein said package and needle and suture are sterile.

25. The package of claim 24 further comprising a sealed outer package.

26. The package of claim 21 wherein the friction plate member additionally comprises a plurality of radially slots extending into the periphery, wherein the slots have an open end and a closed end.

27. The package of claim 21 wherein the inner wall comprises segments separated by spaces.

28. The package of claim 21 wherein the inner wall has a semi-circular cross-section.

29. The package of claim 21 wherein the channel has an oval configuration.

30. A suture package, comprising:

a substantially flat base member having a top side, a bottom side, and an outer periphery;

an outer wall extending upwardly from the top of the base member about the periphery of the base member, said outer wall having a top, an outer surface, and an inner surface;

an inner dispensing wall extending up from the top of the base member said inner wall having an inner side and a top and an outer side and an outer surface, wherein said surface of the dispensing wall and said inner surface of the outer wall and the top of the base member form an endless oval channel for receiving a suture;

a suture wound into the channel such that the suture compresses adjacent coils which do not overlap;

a snap groove extending into the inner surface of the outer wall; and, a flat, floating plate member having a top, a bottom, a central suture discharge opening, and an outer periphery, the flat plate member additionally having biasing means about the outer periphery, wherein the flat friction plate member is mounted on the top of the inner dispensing wall and periphery of the plate member engages the snap groove such that the bottom of the plate member is biased against the top of the inner wall by the biasing means, and wherein the bottom of the plate member is biased against the suture coils;

wherein a suture loaded into the channel is removable through the central discharge opening by displacing the floating plate such that the suture moves between the bottom of the floating plate and the top of the inner wall.

31. The package of claim 30 wherein the biasing means comprises an outwardly extending rim which is curved.

32. The package of claim 30 additionally comprising a surgical needle and suture.

33. The package of claim 32, wherein said package and needle and suture are sterile.

34. The package of claim 33 further comprising a sealed outer package.

35. The package of claim 30 wherein the friction plate member additionally comprises a plurality of radially slots extending into the periphery, wherein the slots have an open end and a closed end.

36. The package of claim 30 wherein the inner wall comprises segments separated by spaces.

37. The package of claim 30 wherein the inner wall has a semi-circular cross-section.

38. The package of claim 30 wherein the channel has an oval configuration.

* * * * *